(12) United States Patent
Ohrbom et al.

(10) Patent No.: US 6,977,309 B2
(45) Date of Patent: Dec. 20, 2005

(54) COMPOUNDS HAVING A SECONDARY OR TERTIARY HYDROXY OF HALIDE GROUP SEPARATED FROM A PRIMARY CARBAMATE GROUP BY THREE OR MORE CARBON ATOMS AND A METHOD OF MAKING THE SAME

(75) Inventors: Walter H. Ohrbom, Hartland Township, MI (US); Craig S. Schang, Madison Heights, MI (US)

(73) Assignee: BASF Corporation, Southfield, MI (US)

( * ) Notice: Subject to any disclaimer, the term of this patent is extended or adjusted under 35 U.S.C. 154(b) by 0 days.

(21) Appl. No.: 10/285,634

(22) Filed: Oct. 31, 2002

(65) Prior Publication Data

US 2004/0087738 A1 May 6, 2004

(51) Int. Cl.$^7$ ............... C07C 269/02; C07C 269/04; C07C 269/06; C07C 271/06; C07C 271/08; C07C 271/10
(52) U.S. Cl. ............... 560/157; 560/166; 560/115; 560/129; 560/155; 560/158
(58) Field of Search .................. 560/157, 166, 560/115, 129, 155, 158

(56) References Cited

U.S. PATENT DOCUMENTS

| | | | |
|---|---|---|---|
| 2,979,514 A | 4/1961 | O'Brien | 260/340.2 |
| 4,301,257 A | 11/1981 | Zengel et al. | 525/329 |
| 4,710,542 A | 12/1987 | Forgione et al. | 525/127 |
| 4,758,632 A | 7/1988 | Parekh et al. | 525/383 |
| 4,939,213 A | 7/1990 | Jacobs, III et al. | 525/329.9 |
| 5,084,541 A | 1/1992 | Jacobs, III et al. | 528/45 |
| 5,288,865 A | 2/1994 | Gupta | 544/200 |
| 5,356,669 A | 10/1994 | Rehfuss et al. | 427/407.1 |
| 5,373,069 A | 12/1994 | Rehfuss et al. | 525/456 |
| 5,474,811 A | 12/1995 | Rehfuss et al. | 427/407.1 |
| 5,512,639 A | 4/1996 | Rehfuss et al. | 525/456 |
| 5,552,497 A | 9/1996 | Taylor et al. | 525/456 |
| 5,605,965 A | 2/1997 | Rehfuss et al. | 525/100 |
| 5,719,237 A | 2/1998 | Rehfuss et al. | 525/419 |
| 5,907,024 A | 5/1999 | Ohrbom et al. | 528/75 |
| 5,945,499 A | 8/1999 | Ohrbom et al. | 528/75 |
| 6,262,297 B1 | 7/2001 | Clements et al. | 560/157 |
| 6,362,285 B1 | 3/2002 | Ohrbom et al. | 525/330.5 |
| 6,580,001 B1 | 6/2003 | Bowman et al. | 558/260 |
| 2002/0123545 A1 | 9/2002 | Yajking et al. | 524/196 |

FOREIGN PATENT DOCUMENTS

| | | | |
|---|---|---|---|
| DE | 1063146 | 7/1958 | ........... C07C/17/01 |
| DE | 1593331 | 10/1966 | |
| DE | 44 32 897 | 3/1996 | ........... C08L/61/20 |
| EP | 245 700 | 4/1987 | ........ C07D/251/54 |
| EP | 594 068 | 10/1993 | ......... C09D/201/02 |
| EP | 594 071 | 10/1993 | ......... C09D/201/02 |
| EP | 594 142 | 10/1993 | ........... C08L/57/12 |
| EP | 604 922 | 12/1993 | ......... C08K/5/3492 |
| EP | 850 986 | 12/1997 | ......... C08K/5/3492 |
| GB | 843331 | 8/1957 | |
| GB | 1068650 | 12/1965 | ......... C07C/125/04 |
| WO | WO94/10211 | 5/1994 | ............. C08F/8/30 |
| WO | WO94/10212 | 5/1994 | ............. C08F/8/30 |
| WO | WO94/10213 | 5/1994 | ............. C08F/8/30 |
| WO | WO 01/56978 | 8/2001 | ........... C08K/5/205 |

OTHER PUBLICATIONS

International Search Report for PCT/US 03/25203, International Filing Date Aug. 13, 2003.
Database CA, Online!, Chemical Abstracts Service, JP 05 138614, Database Accession No. 119:228350 CA, Jun. 8, 1993, XP002265956.
Database CA, Online!, Chemical Abstracts Service, JP 2002 242075, Database Accession No. 137:170974 CA, Aug. 28, 2002, XP002265957.
Database CA, Online!, Chemical Abstracts Service, Database Accession No. 128:206076 CA, 1998, XP002265958.
Database CA, Online!, Chemical Abstracts Service, JP 63 301251, Database Accession No. 111:41492 CA, Jun. 8, 1993, XP002265959.
BASF Coating AG, Docket IN–5605, U.S. Appl. No. 10/182,528, filed Jul. 22, 2002, pp. 1–40.
Marvin L. Green, et al., entitled "Low VOC carbamate functional coatings compositions for automotive topcoats", Mar. 1–3, 2000, New Orleans, LA, USA.
W. Albert Noves, Jr.The Journal of the American Chemical Society, vol. LXXIII, 1951.
English Abstract for DE44 32 897.
Shalom Sarel, et al. Organic Carbonates IV, entitled Factors Affecting Formation of Carbonates Homologous Cyclic, pp. 1873–1878, Dec. 1959.
J. Med. Chem., B. J. Ludwig, et al., entitled Carbamate derivatives related to ,meprobamate, vol. 12, 1969, pp. 462–472.

*Primary Examiner*—Elvis O. Price

(57) ABSTRACT

Provided is a compound having one or more structures of the formula:

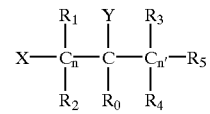

wherein X is a primary carbamate group, Y is a hydroxy or halide group, n is an integer of 2 or more, n' is an integer of 1 or more, and $R_0$, $R_1$, $R_2$, $R_3$, $R_4$ and $R_5$ may be H or a group selected from alkyl groups, aliphatic groups, cycloaliphatic groups, aromatic groups and mixtures thereof, with the provisos that at least one $R_1$ or $R_2$ group is selected from the group consisting of aliphatic groups, cycloaliphatic groups, and aromatic groups, and in substantially all structures primary carbamate group X is attached to a carbon atom having a lower degree of substitution than a carbon atom to which functional group Y is attached. The invention provides a method of making the claimed compound.

30 Claims, No Drawings

COMPOUNDS HAVING A SECONDARY OR TERTIARY HYDROXY OF HALIDE GROUP SEPARATED FROM A PRIMARY CARBAMATE GROUP BY THREE OR MORE CARBON ATOMS AND A METHOD OF MAKING THE SAME

BACKGROUND OF THE INVENTION

Curable coating compositions such as thermoset coatings are widely used in the coatings art. They are often used for topcoats in the automotive and industrial coatings industry.

High-gloss and color-plus-clear composite coatings are particularly useful as topcoats where exceptional gloss, depth of color, distinctness of image, or special metallic effects are desired. The automotive industry has made extensive use of these coatings for automotive body panels. These coatings require an extremely high degree of clarity and a low degree of visual aberrations at the surface of the coating in order to achieve desired visual effects such as a high distinctness of image (DOI).

As a result, high-gloss and composite color-plus-clear coatings are susceptible to a phenomenon known as environmental etch. Environmental etch manifests itself as spots or marks on or in the finish of the coating that often cannot be rubbed out. It is often difficult to predict the degree of resistance to environmental etch that a high gloss or color-plus-clear composite coating will exhibit. Many coating compositions known for their durability and/or weatherability when used in exterior paints, such as high-solids enamels, do not provide the desired level of resistance to environmental etch when used in high gloss coatings and colorplus-clear composite coatings.

Many compositions have been proposed for use as the clearcoat of a color-plusclear composite coating, such as polyurethanes, acid-epoxy systems and the like. However, many prior art systems suffer from disadvantages such as coatability problems, compatibility problems with the pigmented basecoat, solubility problems. Moreover, very few one-pack coating compositions have been found that provide satisfactory resistance to environmental etch, especially in the demanding environment of automotive coatings.

It has been found that carbamate functional polymers such as those described in U.S. Pat. No. 5,356,669 can be used to provide coating compositions which exhibit significantly improved environmental etch resistance. Carbamate functional polymers have been used to provide commercially advantageous coatings compositions, especially as clearcoats in composite color-plus-clear coatings.

Unfortunately, some carbamate functional compounds and/or polymers known in the prior art are vulnerable to instability and decomposition, especially with respect to the formation of cyclic carbonates and carbamates. This results in difficulties in manufacturing and storage.

Moreover, it has heretofore been difficult to make hydroxy functional mono-carbamate functional compounds in an efficient and cost effective manner. In particular, what is desired is a commercially feasible method of making such compounds that utilizes cost effective starting compounds such as polyols and diols.

The prior art has failed to address and rectify these issues.

The preparation of monocarbamate alcohols by the ammonolysis of cyclic carbonates prepared from substituted propanediols is disclosed in *Some Anticonvulsant Agents Derived from 1,3-Propanediols*, Ludwig, B. J. and Piech, E. C.; J. Am Chem. Soc. (1951) 73 5779–81. CAN 47:3228.

U.S. Pat. No. 5,719,237, Rehfuss et al., discloses the use of carbamate functional compounds (a) having a plurality of carbamate groups prepared by a transcarbamylation reaction wherein an alcohol or hydroxylalkyl carbamate is reacted with an alkyl carbamate. The '237 patent teaches that it is desirable to avoid the inclusion of hydroxyl groups in compound (a) as such hydroxyl groups lead to the formation of vulnerable ether bridges.

U.S. Pat. No. 5,907,024, Ohrbom et al., and U.S. Pat. No. 5,945,499 disclose the use of hydroxyalkyl carbamates of the general structure

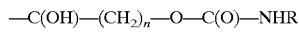

wherein n is an integer from 0 to 6 and R is H or an alkyl group of from 1 to 4 carbons.

U.S. Pat. No. 5,760,127, Bammel et al, and U.S. Pat. No. 6,262,297, Clements et al., disclose hydroxyalkylcarbamate compositions produced by the reaction of anhydrous ammonia or aqueous ammonium hydroxide with a six-membered cyclic carbonate. Bammel et al discloses that five-membered rings are preferred, not as a result of better performance, but as a result of their ease of synthesis and greater degree of commercial availability. Clements et al teaches that six-membered rings are preferred due to increased stability. However, the cost and commercial availability of the six-membered cyclic carbonates renders the process and resultant products to be less than cost effective. Also, depending on the location of any substituent groups on the starting cyclic carbonate, the process disclosed in Clements produces a reaction product which is a compound comprising a mixture of structures with varying reactivity and selectivity.

WO 0156978, Rink, et al discloses positionally isomeric diethyloctanediol dicarbamates and diethyloctanediols diallophanates. The dicarbamate and diallophanate species have no hydroxyl functionality and are made from position isomers of diethyloctane diols.

Despite these and other attempts by the prior art, the prior art has failed to provide a cost effective and efficient manner of making hydroxy functional mono-carbamate functional compounds from polyols and diols. Moreover, the prior art has particularly failed to provide such hydroxy functional mono-carbamate functional compounds that possess improved stability with respect to decomposition and the formation of undesirable cyclic carbonates and carbamates.

Accordingly, it is an object of the invention to provide a reactive compound suitable for use in coating compositions as an additive or reactive diluent or as a reactant to make reactive polymers and/or oligomers. Such a reactive compound should simultaneously provide improvements in reactivity, stability, and reaction selectivity.

In particular, it is an object of the invention to provide reactive compounds having primary carbamate functionality and either halide or hydroxy functionality and that possess improved stability with respect to the decomposition and the formation of undesirable cyclic carbonates and carbamates.

It is a further object of the invention to provide a cost effective and efficient method of making such reactive compounds.

It is a further object of the invention to provide a cost effective and efficient method of using particular polyols and diols to make the desired reactive compounds.

SUMMARY OF THE INVENTION

It has unexpectedly been found that simultaneous improvements in reactivity, stability, and reaction selectivity can be achieved with the use of mono-carbamate functional and mono-hydroxy or halide functional reactive compounds of a particular formula. Indeed, it has been found that a reactive compound comprising one or more structures of the formula:

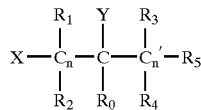

wherein X is a primary carbamate group, Y is a hydroxy group or a halide group, n is an integer of 2 or more, n' is an integer of 1 or more, and $R_0$, $R_1$, $R_2$, $R_3$, $R_4$ and $R_5$ are independently H, an alkyl group, an aromatic group, or mixtures thereof. It is an aspect of the invention that (i) at least one $R_1$ or $R_2$ group is not hydrogen, and (ii) in substantially all structures, primary carbamate group X is attached to a carbon atom having a lower degree of substitution than a carbon atom to which functional group Y is attached.

The reactive compounds of the invention are useful as additives or reactive diluents in curable coating compositions. They are also useful as reactants for making reactive polymers and oligomers suitable for use in curable coating compositions.

With respect to the method of the invention, it has unexpectedly been found that the reaction of compounds (a) and (b) produces mono-hydroxy or halide functional and mono-carbamate functional reactive compounds possessing desirable stability, reactivity and selectivity if compound (a) having functional groups $F_i$ and $F_{ii}$ is selected so as to have at least three carbons atoms separating functional groups $F_i$ and $F_{ii}$, of which functional group $F_{ii}$ is more sterically hindered than functional group $F_i$. In particular, it has been found that compound (a) must be chosen such that functional group $F_i$ is attached to a carbon atom having a lower degree of substitution than that of the carbon atom to which functional group $F_{ii}$ is attached.

Compound (a) is reacted with one or more compounds (b) wherein compound (b) has at least one functional group (iii) reactive with functional group $F_i$ to produce a primary carbamate group. Compounds (a) and (b) are reacted together to produce a reactive compound of the formula:

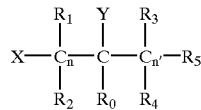

wherein X is a primary carbamate group, Y is a secondary or tertiary hydroxy or halide group, n is an integer of 2 or more, n' is an integer of 1 or more, and $R_0$, $R_1$, $R_2$, $R_3$, $R_4$ and $R_5$ may be H or an alkyl or aromatic containing group, with the provisos that at least one $R_1$ or $R_2$ group is selected from the group consisting of aliphatic groups, cycloaliphatic groups, aromatic groups, and mixtures thereof, and primary carbamate group X is attached to a carbon atom having a lower degree of substitution than that of a carbon atom to which functional group Y is attached.

DETAILS OF THE PREFERRED EMBODIMENTS

The invention provides mono-carbamate functional reactive compounds containing a secondary or tertiary hydroxy or halide group of a particular structure wherein the primary carbamate group and the hydroxy or halide group are separated by three or more carbon atoms. The reactive compounds of the invention possess improved stability, functional selectivity and reactivity.

The invention further provides an economical and efficient method of making the reactive compounds of the invention. The method requires the selection of particular compounds (a) and the reaction therewith of a particular amount of a compound (b).

The reactive compounds of the invention comprise one or more structures of the formula:

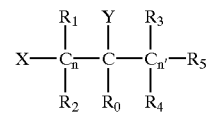

wherein X is a primary carbamate group, Y is a secondary or tertiary hydroxy or halide group, n is an integer of 2 or more, n' is an integer of 1 or more, and $R_0$, $R_1$, $R_2$, $R_3$, $R_4$ and $R_5$ may independently be H or a group selected from aliphatic groups, cycloaliphatic groups, aromatic groups, and mixtures thereof, with the provisos that at least one $R_1$ or $R_2$ group is selected from the group consisting of aliphatic groups, cycloaliphatic groups, and aromatic groups, and primary carbamate group X is attached to a carbon atom having a lower degree of substitution than a carbon atom to which functional group Y is attached.

The term "structures" as used herein refers to isomers that satisfy the requirements of the instant invention. "Isomers" as used herein refers to structural and position isomers that have the same empirical chemical formula. Structures as used herein refers to those isomers which have the same empirical chemical formula but which satisfy the requirements of the instant formula. For the purposes of the instant invention, it will be appreciated that a single compound may comprise one or more than one structure. Illustrative examples of structural isomers are 2-ethyl-1,3-hexanediol and 2-propyl-1,3-pentanediol. Illustrative examples of position isomers are 2-ethyl-1,3-hexanediol and 2-ethyl-1,4-hexanediol. Illustrative examples of isomers which are both structural and position isomers are 2-ethyl-1,3-hexanediol and 2-propyl-1,4-pentanediol. However, it will be appreciated that only those isomers that satisfy the requirements of the instant invention may be structures of the reactive compound of the invention, i.e., they must (1) be of the formula:

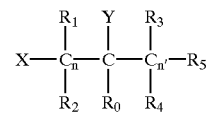

wherein X is a primary carbamate group, Y is either a hydroxy group or a halide group, n is an integer of 2 or more, n' is an integer of 1 or more, and $R_0$, $R_1$, $R_2$, $R_3$, $R_4$ and $R_5$ are independently H, an alkyl group, an aromatic group, or mixtures thereof, (2) at least one $R_1$ or $R_2$ group in this formula must not be hydrogen, and (3) most importantly, primary carbamate group X must be attached to a carbon atom having a lower degree of substitution than the carbon atom to which functional group Y is attached.

In general, the reactive compound of the invention may comprise one or more structures that satisfy the above requirements. In a preferred embodiment, the reactive compound will comprise at least two structures that are isomerically different as defined above but which each satisfy the above noted requirements of the invention. In a most preferred embodiment of the invention, the reactive compound of the invention will comprise at least four structures.

As noted above, it is an aspect of the invention that primary carbamate group X be attached to a carbon atom having a lower degree of substitution than the carbon atom to which functional group Y is attached. The term "lower degree of substitution" may be understood per the following statements. If X is a primary carbamate group attached to a primary carbon atom (i.e., X—$CH_2$—), Y will be functional group attached to either a secondary carbon atom (i.e., —Cn-CH(Y)—Cn'-) or a tertiary carbon atom (i.e., —Cn-$CR_0$(Y)—Cn'-wherein $R_0$ is not hydrogen and is an alkyl or aromatic containing group as further defined herein. If X is a primary carbamate group attached to a secondary carbon atom, i.e., (X—CHR—, wherein R is either $R_1$ or $R_2$ as defined above but is not hydrogen), Y must be a functional group attached to a tertiary carbon (i.e., —Cn-$CR_0$(Y)—Cn'-wherein $R_0$ is as defined above but is not hydrogen). It can be appreciated that because primary carbamate group X must be attached to a carbon atom having at least one fewer non-hydrogen substituent than that of the carbon atom to which functional group Y is attached, at least one of the substituents $R_1$ and $R_2$ must be hydrogen for the carbon to which X is attached.

As used herein, "primary carbamate group" refers to the functional group having the structure

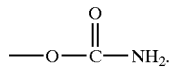

Thus, the primary carbamate group of the invention may be defined as a terminal or pendent carbamate group. In addition, it is an aspect of the method of the invention that the resultant reactive compounds will have one and only one primary carbamate group. That is, the reactive compounds produced by the instant method are limited to monocarbamate functional compounds having at least one additional functional group that is either secondary or tertiary.

Reactive compounds made by the method of the invention will be substantially free of heteratoms. "Heteroatoms" as used herein refers to atoms other than carbon or hydrogen. The phrase "substantially free of" as used herein means that the portion of reactive compound which does not include the primary carbamate group X or the secondary or tertiary functional group Y will generally have no than two atoms which are other than carbon or hydrogen, i.e., atoms such as N, O, Si, mixtures thereof, and the like. More preferably, that portion of reactive compound that does not include primary carbamate group X or tertiary or secondary functional group Y will have no more than one atom that is other than carbon or hydrogen. In a most preferred embodiment, that portion of reactive compound that does not include functional groups X and Y will have no heteratoms, i.e., will consist solely of carbon and hydrogen atoms. Thus, in a most preferred aspect of the invention, the only heteratoms in reactive compound will be present in functional groups X and Y.

Functional group Y could be any group convertible to a carbamate group but may not be a carbamate group. Functional group Y will preferably be a hydroxyl group or halide groups. Hydroxyl groups are most preferred for use as functional group Y.

It will be appreciated that functional group Y is not located on a primary carbon atom in the above formula. Rather, functional group Y will be a secondary functional group when $R_0$ is H and will be a tertiary functional group when $R_0$ is an alkyl or aromatic containing group, i.e., an aliphatic group, a cycloaliphatic group, an aromatic group, or mixtures thereof. In a most preferred embodiment Y will be a secondary functional group and $R_0$ will be hydrogen.

In general, $R_0$, $R_1$, $R_2$, $R_3$, $R_4$ and $R_5$ may be H or an alkyl group, an aromatic group, or mixtures thereof Illustrative alkyl groups are aliphatic groups and cycloaliphatic groups. Suitable alkyl and aromatic containing groups will generally have from one to sixteen carbon atoms and may be linear or branched. As used herein, the term "branched" refers to both lateral branches and forked branches. Lateral refers to a branch of two small chains at the end atom of a carbon chain. Forked refers to a branch of two small chains in the middle of a carbon chain. Any individual substituent may have both branching and forking therein. In addition, it is within the scope of the invention for two or more of the various R substituents to be connected with each other.

As noted above $R_0$ may be H or an alkyl or aromatic group containing substituent. In a most preferred embodiment $R_0$ will be H so that functional group Y is a secondary functional group. If $R_0$ is not hydrogen, suitable groups are those groups selected from the group of aliphatic groups, cycloaliphatic groups, aromatic groups and mixtures thereof. Preferred for use as $R_0$ are aliphatic and cycloaliphatic groups, with aliphatic groups being most preferred for use as $R_0$. Particularly suitable groups for use as $R_0$ are aliphatic groups and cycloaliphatic groups containing from one to sixteen carbon atoms, with aliphatic groups containing one to twelve carbon atoms being preferred if $R_0$ is an alkyl group and aliphatic groups containing one to eight carbon atoms being most preferred if $R_0$ is an alkyl group. Finally, it is within the scope of the invention that $R_0$ be an alkyl or aromatic group connected to any of the other $R_{1-5}$ substituents.

$R_1$, $R_2$, $R_3$, $R_4$ and $R_5$ may be H or a group as defined above for $R_0$.

However, it is an aspect of the invention that at least one $R_1$ or $R_2$ group must be selected from the group consisting of aliphatic groups, cycloaliphatic groups, aromatic groups, and mixtures thereof. That is, at least one of the $R_1$ and $R_2$ substituent groups must be other than hydrogen so long as primary carbamate group X is attached to a carbon atom having a lower degree of substitution than the carbon atom to which functional group Y is attached. Illustrative groups suitable for use as the $R_1$ or $R_2$ group that is not hydrogen are as defined above for $R_0$. Preferred for use as $R_1$ and $R_2$ are aliphatic and cycloaliphatic groups, with aliphatic groups being most preferred for use as $R_1$ or $R_2$ if they are not hydrogen Particularly suitable non-hydrogen groups for use as $R_1$ and $R_2$ are aliphatic groups and cycloaliphatic groups containing from one to sixteen carbon atoms, with aliphatic groups containing from one to twelve carbon atoms being preferred if $R_1$ or $R_2$ is an alkyl group and aliphatic groups containing one to eight carbon atoms being most preferred if $R_1$ or $R_2$ is an alkyl group. Finally, it is within the scope of the invention that $R_1$ or $R_2$ be an alkyl or aromatic group connected to any of the other $R_{0, 3-5}$ substituents.

As noted above, because primary carbamate group X must be attached to a carbon atom having a lower degree of substitution than the carbon atom to which functional group Y is attached, at least one of the substituents $R_1$ and $R_2$ must be hydrogen for the carbon to which X is attached. This requirement is consistent with the requirement that at least one $R_1$ or $R_2$ group must be selected from the group consisting of aliphatic groups, cycloaliphatic groups, aromatic groups and mixtures thereof. When n is 2 and $R_0$ is not hydrogen, the at least one $R_1$ or $R_2$ group that is not hydrogen may be a substituent of the carbon immediately adjacent to the carbon attached to the primary carbamate group X. That is, the carbon to which the carbamate group is attached may have a primary or secondary degree of substitution. When n is greater than 2 and $R_0$ is not hydrogen, the at least one $R_1$ or $R_2$ group that is not hydrogen may be a substituent of the carbon to which the carbamate group is attached or to any of the carbons between the carbon attached to the primary carbamate group X and the carbon attached to the functional group Y, i.e., the $C_n$ carbons.

However, it is preferred that the at least one $R_1$ or $R_2$ group which is not hydrogen be attached to a carbon not directly attached to the carbamate group X. More preferably, the at least one $R_1$ or $R_2$ group that is not hydrogen will preferably be attached to a carbon atom located in closer proximity to functional group Y rather than functional X. When n is two, it will be appreciated that the at least one $R_1$ or $R_2$ group which is not hydrogen will most preferably be attached to a carbon atom located an equal distance between the carbons to which the functional groups X and Y are attached. When n is three or greater, the at least one $R_1$ or $R_2$ group which is not hydrogen will most preferably be attached to the carbon atom which is adjacent to the carbon atom to which the functional Y is attached or be in closer proximity thereto than to the carbon atom to which functional group X is attached.

It is another aspect of the invention that n be an integer of 2 or more so that functional groups X and Y are separated by at least three carbon atoms, including the carbon atoms to which are attached the functional groups X and Y. In one preferred embodiment of the invention, n will be an integer of from 2 to 12, more preferably from 2 to 8, and most preferably from 2 to 4. In another embodiment of the invention, n will be an integer of at least 3, more preferably from 3 to 12, and most preferably from 3 to 4.

In the reactive compound produced by the method of the invention, n' must be an integer of 1 or more and may not be 0. In a preferred embodiment of the invention, n' will be an integer of from 1 to 16, more preferably from 1 to 12, and most preferably n' will be an integer of from 1 to 8.

$R_3$, $R_4$ and $R_5$ are selected from the group consisting of H, $C_1$–$C_{16}$ aliphatic groups, cycloaliphatic groups, aromatic groups, and mixtures thereof. In a preferred embodiment of the invention, $R_3$, $R_4$ and $R_5$ may be selected from the group consisting of H, aliphatic groups, cycloaliphatic groups, and mixtures thereof. In a most preferred embodiment, $R_3$, $R_4$ and $R_5$ will be selected from the group consisting of H, aliphatic groups, and mixtures thereof. In one embodiment according to the invention, $R_3$, $R_4$ and $R_5$ may be connected to $C_{n'}$, $R_0$, $R_1$ or $R_2$ to form a cyclic ring.

It is another aspect of the invention that in general, it is preferred that at least one of $R_3$, $R_4$ and $R_5$ will be a group other than hydrogen when n' is greater than 1. In a preferred embodiment, at least two of $R_3$, $R_4$ and $R_5$ will be other than hydrogen, i.e., $C_1$–$C_{16}$ aliphatic groups, cycloaliphatic groups, aromatic groups, and mixtures thereof, when n' is greater than 1. In a most preferred embodiment of the invention, when n' is greater than one, at least three of $R_3$, $R_4$ and $R_5$ will be selected from the group of $C_1$–$C_{16}$ aliphatic groups, cycloaliphatic groups, aromatic groups, and mixtures thereof.

In a most preferred embodiment, the reactive compounds of the invention will be made by the method of the invention. It is a particular advantage of the method of the invention that in the resulting reaction product substantially all of the structures therein possess a primary carbamate group X attached to a carbon atom having a lower degree of substitution than the carbon atom to which functional group Y is attached. It is a particular disadvantage of prior art processes that they fail to provide such a reaction product.

As used herein, "substantially" refers to no more than 10% of the resulting mono-carbamate functional reaction product has a primary carbamate group attached to a carbon atom having a degree of substitution that is equal to or higher than that of the carbon atom to which the Y functional group is attached, preferably no more than 7%, and most preferably no more than 3%. It will be appreciated that amounts of unreacted starting materials are not part of this calculation.

The method of the invention requires that the reactive compounds of the invention be made by reacting a compound (a) and a compound (b).

Compound (a) must have a functional group $F_i$ and a functional group $F_{ii}$ separated by at least three carbon atoms, wherein said functional groups $F_i$ and $F_{ii}$ are independently selected from the group consisting of functional groups convertible to primary carbamate groups, and functional group $F_i$ is attached to a carbon atom having a lower degree of substitution than a carbon atom to which functional group $F_{ii}$ is attached.

Functional groups $F_i$ and $F_{ii}$ are each independently selected from the group of functional groups convertible to primary carbamate groups. Preferred examples of functional groups $F_i$ and $F_{ii}$ convertible to primary carbamate groups are hydroxy groups and halide groups. Suitable halide groups include chloride, bromide, and iodide, with chloride being the most favored halide. Most preferably functional groups $F_i$ and $F_{ii}$ will be hydroxyl groups.

Suitable compounds (a) may include polyols, diols, polyhalides, and dihalides. However, the use of diols and dihalides as compound (a) is especially preferred as they are the most commercially available and economically feasible. Diols are most preferred for use as compound (a). Indeed, it is a particular benefit of the invention that it provides an economical and commercially feasible method of making thermally stable mono-carbamate compounds containing at least one functional group from compound (a) starting materials selected from the group consisting of dihalides and diols.

In a most preferred embodiment, compound (a) will be selected from the group of diols and dihalides of the following formula:

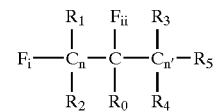

wherein $F_i$ and $F_{ii}$ are hydroxy or halide functional groups, n is an integer of 2 or more, n' is an integer of 1 or more, and $R_0$, $R_1$, $R_2$, $R_3$, $R_4$ and $R_5$ may individually be H or a group selected from the group of $C_1$–$C_{16}$ aliphatic groups, cycloaliphatic groups, aromatic groups, and mixtures thereof. However, it is an aspect of the invention that at least one $R_1$ or $R_2$ group be selected from the group consisting of $C_1$–$C_{16}$ aliphatic groups, cycloaliphatic groups, aromatic groups, and mixtures thereof Functional group $F_i$ must be attached to a carbon atom having a lower degree of substitution than that of the carbon atom to which functional group $F_{ii}$ is attached.

Thus, it is an important aspect of the method of the invention that in compound (a), functional group $F_i$ will be attached to a carbon atom having a lower degree of substitution than the carbon atom to which functional group $F_{ii}$ is attached. For example, if $F_i$ is a primary functional group attached to a primary carbon atom (i.e., X—CH$_2$—), $F_{ii}$ will be functional group attached to either a secondary carbon atom (i.e., —C$_n$—CH(Y)—C$_{n'}$—) or a tertiary carbon atom (i.e., —C$_n$—CR$_0$(Y)—C$_{n'}$—wherein R$_0$ is not hydrogen and is as defined above). If $F_1$ is a primary functional group attached to a secondary carbon atom, i.e., (X—CHR—, wherein R is either $R_1$ or $R_2$ as defined above but is not hydrogen), $F_{ii}$ must be a functional group attached to a tertiary carbon, (i.e., —C$_n$—CR$_0$(Y)—C— wherein R$_0$ is not hydrogen and is as defined above). It can be appreciated that because functional group $F_i$ must be attached to a carbon atom having a lower degree of substitution than the carbon atom to which functional group $F_{ii}$ is attached, at least one of the substituents $R_1$ and $R_2$ on the carbon to which $F_i$ is attached must be hydrogen.

Most preferred compounds (a) will be substantially free of heteroatoms. "Heteroatoms" as used herein refers to atoms other than carbon or hydrogen. The phrase "substantially free of" as used herein means that the portion of compound (a) which does not include the functional groups $F_i$ and $F_{ii}$ will generally have no than two atoms which are other than carbon or hydrogen, i.e., atoms such as N, O, Si, mixtures thereof, and the like. More preferably, that portion of compound (a) that does not include functional groups $F_i$ and $F_{ii}$ will have no more than one atom that is other than carbon or hydrogen. In a most preferred embodiment, that portion of compound (a) that does not include functional groups $F_i$ and $F_{ii}$ will have no heteroatoms, i.e., will consist solely of carbon and hydrogen atoms. Thus, in a most preferred aspect of the invention, the only heteroatoms in compound (a) will be present in functional groups $F_i$ and $F_{ii}$.

It will be appreciated that functional group $F_{ii}$ is not located on a primary carbon atom in the above formula. Rather, functional group $F_{ii}$ will be a secondary functional group when $R_0$ is H and will be a tertiary functional group when $R_0$ is not hydrogen and is selected from the group of aliphatic groups, cycloaliphatic groups, aromatic groups, or mixtures thereof. In a most preferred embodiment $F_{ii}$ will be a secondary functional group and $R_0$ will be hydrogen.

In general, $R_0$, $R_1$, $R_2$, $R_3$, $R_4$ and $R_5$ may be H or an alkyl group, an aromatic group, or mixtures thereof. Illustrative alkyl groups are aliphatic groups and cycloaliphatic groups. Suitable alkyl and aromatic containing groups will generally have from one to sixteen carbon atoms and may be linear or branched. As used herein, the term "branched" refers to both lateral branches and forked branches. Lateral refers to a branch of two small chains at the end atom of a carbon chain. Forked refers to a branch of two small chains in the middle of a carbon chain. Any individual substituent may have both branching and forking therein. In addition, it is within the scope of the invention for two or more of the various R substituents to be connected with each other.

As noted above $R_0$ may be H or an alkyl or aromatic containing group or mixtures thereof. In a most preferred embodiment $R_0$ will be H so that functional group $F_{ii}$ is a secondary functional group. If $R_0$ is not hydrogen, suitable groups are those groups selected from the group of aliphatic groups, cycloaliphatic groups, aromatic groups and mixtures thereof. Preferred for use as $R_0$ are aliphatic and cycloaliphatic groups, with aliphatic groups being most preferred for use as $R_0$ Particularly suitable groups for use as $R_0$ are aliphatic groups and cycloaliphatic groups containing from one to sixteen carbon atoms, with aliphatic groups containing one to twelve carbon atoms being preferred if $R_0$ is an alkyl group and aliphatic groups containing one to eight carbon atoms being most preferred if $R_0$ is an alkyl group. Finally, it is within the scope of the invention that $R_0$ be an alkyl or aromatic group connected to any of the other $R_{1-5}$ substituents.

$R_1$, $R_2$, $R_3$, $R_4$ and $R_5$ may be H or a group as defined above for $R_0$.

However, it is an aspect of the invention that at least one $R_1$ or $R_2$ group must be selected from the group consisting of aliphatic groups, cycloaliphatic groups, and aromatic groups. That is, at least one of the $R_1$ and $R_2$ substituent groups must be other than hydrogen so long as functional group $F_i$ is attached to a carbon atom having a lower degree of substitution than the carbon atom to which functional group $F_{ii}$ is attached. Illustrative groups suitable for use as the $R_1$ or $R_2$ groups that are not hydrogen are those as defined above for $R_0$. Preferred for use as $R_1$ and $R_2$ are aliphatic and cycloaliphatic groups, with aliphatic groups being most preferred for use as $R_1$ or $R_2$ if they are not hydrogen Particularly suitable non-hydrogen groups for use as $R_1$ and $R_2$ are aliphatic groups and cycloaliphatic groups containing from one to sixteen carbon atoms, with aliphatic groups containing from one to twelve carbon atoms being preferred if $R_1$ or $R_2$ is an alkyl group and aliphatic groups containing one to eight carbon atoms being most preferred if $R_1$ or $R_2$ is an alkyl group. Finally, it is within the scope of the invention that $R_1$ or $R_2$ be an alkyl or aromatic group connected to any of the other $R_{0,\ 3\text{-}5}$ substituents.

As noted above, because functional group $F_i$ must be attached to a carbon atom having a lower degree of substitution than the carbon atom to which functional group $F_{ii}$ is attached, at least one of the substituents $R_1$ and $R_2$ must be hydrogen for the carbon to which $F_i$ is attached. This requirement is consistent with the requirement that at least one $R_1$ or $R_2$ group must be selected from the group consisting of aliphatic groups, cycloaliphatic groups, aromatic groups and mixtures thereof. When n is 2 and $R_0$ is not hydrogen, the at least one $R_1$ or $R_2$ group that is not hydrogen may be a substituent of the carbon immediately adjacent to the carbon attached to the primary carbamate group X. That is, the carbon to which the carbamate group is attached may have a primary or secondary degree of substitution. When n is greater than 2 and $R_0$ is not hydrogen, the at least one $R_1$ or $R_2$ group that is not hydrogen may be a substituent of the carbon to which the carbamate group is attached or to any of the carbons between the carbon attached to the functional group $F_i$ and the carbon attached to the functional group $F_{ii}$, i.e., the $C_n$ carbons.

However, it is preferred that the at least one $R_1$ or $R_2$ group which is not hydrogen be attached to a carbon not directly attached to the functional group $F_i$. More preferably, the at least one $R_1$ or $R_2$ group that is not hydrogen will preferably be attached to a carbon atom located in closer proximity to functional group $F_{ii}$ rather than functional group $F_i$. When n is two, it will be appreciated that the at least one $R_1$ or $R_2$ group which is not hydrogen will most preferably be attached to a carbon atom located an equal distance between the carbons to which the functional groups $F_i$ and $F_{ii}$ are attached. When n is three or greater, the at least one $R_1$ or $R_2$ group which is not hydrogen will most preferably be attached to the carbon atom which is adjacent to the carbon atom to which the functional group $F_{ii}$ is attached or be in close proximity thereto than to the carbon atom to which the functional group $F_i$ is attached.

It is another aspect of the invention that n be an integer of 2 or more so that functional groups $F_i$ and $F_{ii}$ are separated by at least three carbon atoms, including the carbon atoms to which are attached the functional groups $F_i$ and $F_{ii}$. In one preferred embodiment of the invention, n will be an integer of from 2 to 12, more preferably from 2 to 8, and most preferably from 2 to 4. In another embodiment of the invention, n will be an integer of at least 3, more preferably from 3 to 12, and most preferably from 3 to 4.

In the most preferred compound (a) used in the method of the invention, n' must be an integer of 1 or more and may not be 0. In a preferred embodiment of the invention, n' will be an integer of from 1 to 16, more preferably from 1 to 12, and most preferably n' will be an integer of from 2 to 8.

$R_3$, $R_4$ and $R_5$ are selected from the group consisting of H, $C_1$–$C_{16}$ aliphatic groups, cycloaliphatic groups, aromatic groups, and mixtures thereof. In a preferred embodiment of the invention, $R_3$, $R_4$ and $R_5$ may be selected from the group consisting of H, aliphatic groups, cycloaliphatic groups, and mixtures thereof. In a most preferred embodiment, $R_3$, $R_4$ and $R_5$ will be selected from the group consisting of H, aliphatic groups, and mixtures thereof. In one embodiment according to the invention, $R_3$, $R_4$ and $R_5$ may be connected to $C_{n'}$, $R_0$, $R_1$ or $R_2$ to form a cyclic ring.

It is another aspect of the invention that in general, it is preferred that at least one of $R_3$, $R_4$ and $R_5$ will be a group other than hydrogen when n' is greater than 1. In a preferred embodiment, at least two of $R_3$, $R_4$ and $R_5$ will be other than hydrogen, i.e., $C_1$–$C_{16}$ aliphatic groups, cycloaliphatic groups, aromatic groups, and mixtures thereof, when n' is greater than 1. In a most preferred embodiment of the invention, when n' is greater than one, at least three of $R_3$, $R_4$ and $R_5$ will be selected from the group of $C_1$–$C_{16}$ aliphatic groups, cycloaliphatic groups, aromatic groups, and mixtures thereof.

Illustrative compounds (a) for use in a preferred embodiment of the method of the invention include 2-ethyl-1,3 hexanediol, 2-methyl-2,4-pentane diol, 2,2,4-trimethyl-1,3-pentanediol, 2,4-diethyl-1,5-octanediol, 1-hydroxymethyl cyclohexan-4-ol, and all those isomers thereof which satisfy the above requirements of the preferred formula for compound (a).

"Isomers" as used herein refers to structural and position isomers that have the same empirical chemical formula. An illustrative example of some structural isomers would be 2-ethyl-1,3-hexanediol and 2-propyl-1,3-pentanediol. An illustrative example of a position isomer would be 2-ethyl-1,3-hexanediol and 2-ethyl-1,4-hexanediol. An illustrative example of isomers which are both structural and position isomers would be 2-ethyl-1,3-hexanediol and 2-propyl-1,4-pentanediol. However, it will be appreciated that only those isomers that satisfy the requirements of the instant invention are suitable, i.e., they must (1) be of the formula:

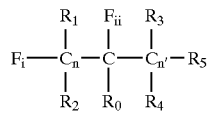

wherein $F_i$ and $F_{ii}$ are either hydroxy groups or halide groups, n is an integer of 2 or more, n' is an integer of 1 or more, and $R_0$, $R_1$, $R_2$, $R_3$, $R_4$ and $R_5$ are independently H, an alkyl group, an aromatic group, or mixtures thereof, (2) at least one $R_1$ or $R_2$ group in this formula must not be hydrogen, and (3) most importantly, functional group $F_i$ must be attached to a carbon atom having a lower degree of substitution than the carbon atom to which functional group $F_{ii}$ is attached.

In one preferred embodiment, compound (a) will be selected from those members of the preferred formula for compound (a) that possess a particularly preferred isomeric distribution. 'Isomeric distribution' as used herein refers to the number of individual isomers that make up the material. A particularly preferred isomeric distribution is one in which compound (a) is a mixture of isomers having at least 4 or more individual isomers or structures. The resulting products made according to the invention from these materials have a greater tendency of being non-crystalline in nature. This is of advantage for obtaining low VOC coatings.

However, it will be appreciated that even compounds (a) consisting of one structure or isomer will provide acceptable levels of performance with respect to low VOC coatings. While not wishing to be bound to a particular theory, it is believed that this is attributable to the low degree of symmetry found in particular compounds (a) and thus in the final reactive compounds of the invention.

It will be appreciated that the selection of compound (b) is somewhat dependent upon the selection of functional groups $F_i$ and $F_{ii}$ of compound (a). In general, if functional group (i) is a hydroxyl group, it will be converted into a primary carbamate by reaction with a compound (b) selected from the group consisting of alkyl carbamates, cycloalkyl carbamates, ether carbamates, beta hydroxy alkyl carbamates, aryl carbamates, cyanic acid produced, for example, by the decomposition of urea, and phosgene followed by reaction with ammonia. If functional group (i) is a halide group, it may be converted into a primary carbamate group by reaction with a metal carbamate such as silver carbamate as discussed in P. Adams & F. Baron, "Esters of Carbamic Acid", Chemical Review, v. 65, 1965. In a preferred embodiment, compound (b) will be selected from the group of alkyl carbamates, cycloalkyl carbamates, ether carbamates and aryl carbamates, and mixtures thereof, with alkyl carbamates being most preferred as compound (b).

Illustrative alkyl carbamates, cycloalkyl carbamates, and aryl carbamates include methyl carbamate, propyl carbamate, n-butylcarbamate, cyclohexyl carbamate, t-butyl carbamate, isopropyl carbamate, and phenyl carbamate. An example of a hydroxy alkyl carbamate is hydroxy ethyl carbamat. An example of an ether carbamate is 2-methoxyethyl carbamate. It will be appreciated that when (b) is selected from these compounds, reaction with suitable compounds (a) results in alcohols, phenols, ether alcohols and related materials as by-products. Examples of most preferred alkyl carbamates for use as compound (b) include methyl carbamate, isopropyl carbamate and n-butyl carbamate.

Compound (a) and compound (b) are reacted under conditions intended to minimize the formation of functional group $F_{ii}$ to a carbamate group. In general, compounds (a) and (b) will reacted under conditions such that no more than 10% of the functional group $F_{ii}$ is converted to a carbamate group, based on the starting amount of compound (a). More preferably, compounds (a) and (b) will be reacted under conditions such that no more than 5% of functional group $F_{ii}$ is converted to a carbamate group, and most preferably no more than 4% of functional group $F_{ii}$ will be converted to a carbamate group, all based on the starting amount of compound (a).

Thus, the formation of dicarbamate species is highly disfavored in the method of the invention. One technique to disfavor the formation of the dicarbamate is to use a deficit amount of compound (b), that is, the equivalent of the functional groups of compound (b) is less than the equivalent amount of functional group $F_i$ based on the starting amount of compound (a). In this case, the equivalent amount of compound (b) used in relationship to functional group $F_i$ can range from 0.99 to 1. An alternative technique that can be used to disfavor the formation of the dicarbamate when one or more than one equivalent of compound (b) are used in comparison to functional group $F_i$ on compound (a) is to stop the reaction before all of functional $F_i$ is converted to a primary carbamate. This second technique works best for reaction conditions that have a high degree of selectivity such as transcarbamation reactions. In comparison, this technique would be disfavored in a more nonselective reaction such as that between a hydroxy group and isocyanic acid.

While not wishing to be bound to a particular theory, it is believed that the effectiveness of these two approaches can be increased by increasing the relative degree of steric hindrance surrounding functional groups $F_i$ and $F_{ii}$ on compound (a). That is, in general, dicarbamate formation can be diminished if the degree of steric hindrance surrounding functional group $F_{ii}$ is greater than the degree of steric hindrance on functional group $F_i$ This relationship is believed to hold true regardless of the method of reaction selected.

If not all of functional group $F_i$ has been transformed into a primary carbamate, the excess amount of unreacted starting material (a) can be removed by known techniques, such as vacuum distillation, extraction or filtration or may be left in as discussed below.

The resultant reactive compound may be used in a variety of compositions used in film-forming applications, including but not limited to curable coating compositions, sealant compositions, and adhesive compositions. The reactive compound of the invention may be used as a film-forming component of such compositions, as a reactive diluent that may replace some or all traditional solvents, or may alternatively be used as a reactant to form polymeric and oligomeric components for use in such compositions, or combinations thereof.

In some cases, the presence of unreacted (a) in the reactive compound of the invention may be desirable for the formation of other polymeric products, especially when reactive compound is used as a reactant to make such polymeric or oligomeric materials. An example is discussed in U.S. Pat. No. 5,676,069, Rehfuss, et al, where unreacted polyol can function as a chain extender. In other cases, the presence of unreacted (a) can be used to make a dual hydroxy carbamate material, such as described in U.S. Pat. No. 5,907,024, Ohrbom, et al, and U.S. Pat. No. 6,080,825.

When the reactive compound of the invention is used as a part of a coating composition, any excess amount of unreacted (a) may first be removed as described above, or it can be left in as a component of the final coating composition. If left in the final coating composition, the presence of unreacted (a) can act as a solvent, a reactive diluent or both.

The invention is further described in the following examples. All parts and percentages are by weight unless otherwise specified.

EXAMPLES

Example 1

Preparation of the Reactive Compound by the Method of the Invention

A mixture of 55.69 parts of 2-ethyl-1,3-hexanediol, 20.94 parts of methyl carbamate, 23.26 parts of toluene and 0.07 parts of dibutyl tin oxide were heated under an inert atmosphere to reflux in a reactor equipped with an extractor that can remove methanol but returns toluene to the reaction mixture. Once at reflux, the inert atmosphere was turned off. An additional 0.04 parts of dibutyl tin oxide was added after the first three hours at reflux. Additional toluene was added to the reaction mixture to keep the reflux temperature below 130° C. The reaction was stopped when ~85% of the theoretical amount of hydroxy groups were converted into carbamate groups. Free methyl carbamate, toluene and some of the unconverted 2-ethyl-1,3-hexanediol was then removed by vacuum distillation. The final product was a mixture of 55.5% 2-ethyl-1,3-hexanediol, 42.3% 3-hydroxy-2-ethyl carbamate and 2.2% 2-ethylhexane1,3-dicarbamate.

Example 2

Preparation of the Reactive Compound by the Method of the Invention

A mixture of 45.52 parts of 2-ethyl-1,3-hexanediol, 23.4 parts of methyl carbamate, 0.08 parts butyltin hydroxide oxide and 30.4 parts toluene was headed heated under an inert atmosphere to reflux in a reactor equipped with an extractor that can remove methanol but return toluene to the reaction mixture. Once at reflux, the inert atmosphere was turned off. The reaction was stopped when approximately half of the theoretical amount of mono-carbamate product was formed. Then 0.6 parts of octanethiol was added and the reaction mixture was held at 100° C. for 1.5 hours. Free methyl carbamate, toluene, octanethiol and some of the unconverted 2-ethyl-1,3-hexanediol was then removed by vacuum distillation. The final product was a mixture of 43.0% 2-ethyl-1,3-hexanediol and 53.2% 3-hydroxy-2-ethylhexane carbamate and 3.7% 2-ethyl-1,3-hexane dicarbamate.

What is claimed is:

1. A reactive compound comprising one or more structures of the formula:

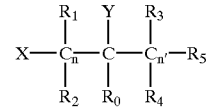

wherein
X is a primary carbamate group,
Y is a hydroxy group or a halide group,
n is an integer of at least 3,
n' is an integer of 1 or more, and
$R_0$, $R_1$, $R_2$, $R_3$, $R_4$ and $R_5$ are independently H, an alkyl group, an aromatic group, or mixtures thereof,
with the provisos that
(i) at least one $R_1$ or $R_2$ group is not hydrogen, and
(ii) in substantially all structures, primary carbamate group X is attached to a carbon atom having a lower degree of substitution than a carbon atom to which functional group Y is attached.

2. The reactive compound of claim 1 comprising one structure.

3. The reactive compound of claim 2 comprising at least two structures.

4. The reactive compound of claim 3 comprising at least four structures.

5. The reactive compound of claim 1 wherein Y is a hydroxy group.

6. The reactive compound of claim 1 wherein n is an integer of from 3 to 12.

7. The reactive compound of claim 6 wherein n is an integer of from 3 to 8.

8. The reactive compound of claim 7 wherein n is an integer of from 3 to 4.

9. The reactive compound of claim 1 wherein n' is 1 to 12.

10. The reactive compound of claim 1 wherein n' is 1 to 8.

11. The reactive compound of claim 1 wherein at least one of the substituents $R_1$ and $R_2$ on the carbon to which X is attached is hydrogen.

12. The reactive compound of claim 11 wherein both of the substituents $R_1$ and $R_2$ on the carbon to which X is attached are hydrogen.

13. The reactive compound of claim 12 wherein $R_0$ is H.

14. The reactive compound of claim 12 wherein $R_0$ is not hydrogen.

15. The reactive compound of claim 13 wherein $R_0$ is selected from the group consisting of $C_1$–$C_z$ aliphatic groups, $C_1$–$C_{16}$ cycloaliphatic groups, $C_1$–$C_{16}$ aromatic groups, and mixtures thereof.

16. The reactive compound of claim 14 wherein $R_0$ is selected from the group consisting of $C_1$–$C_{12}$ aliphatic groups.

17. The reactive compound of claim 14 wherein $R_0$ is selected from the group consisting of $C_1$–$C_8$ aliphatic groups.

18. The reactive compound of claim 11 wherein at least one of the substituents $R_1$ and $R_2$ on the carbon to which X is attached is not hydrogen and $R_0$ is not hydrogen.

19. The reactive compound of claim 18 wherein at least one of the $R_1$ or $R_2$ groups on the carbon to which X is attached is selected from the group consisting of $C_1$–$C_{16}$ aliphatic groups, $C_1$–$C_{16}$ cycloaliphatic groups, $C_1$–$C_{16}$ aromatic groups and mixtures thereof.

20. The reactive compound of claim 18 wherein $R_0$ is selected from the group consisting of $C_1$–$C_{16}$ aliphatic groups, $C_1$–$C_{16}$ cycloaliphatic groups, $C_1$–$C_{16}$ aromatic groups, and mixtures thereof.

21. The reactive compound of claim 20 wherein $R_0$ is selected from the group consisting of $C_1$–$C_{12}$ aliphatic groups.

22. The reactive compound of claim 21 wherein $R_0$ is selected from the group consisting of $C_1$–$C_8$ aliphatic groups.

23. The reactive compound of claim 1 wherein the at least one $R_1$ or $R_2$ group that is not hydrogen is attached to a carbon atom located in closer proximity to the carbon atom to which functional group Y is attached than to the carbon atom to which functional group X is attached.

24. The reactive compound of claim 1 wherein n is 3 or greater and the at least one $R_1$ or $R_2$ group that is not hydrogen is attached to a carbon atom located in closer proximity to the carbon atom to which functional group Y is attached than to the carbon atom to which functional group X is attached.

25. The reactive compound of claim 24 wherein n is 3 or greater and the at least one $R_1$ or $R_2$ group that is not hydrogen is attached to a carbon atom which is adjacent to the carbon atom to which functional group Y is attached.

26. The reactive compound of claim 1 wherein $R_3$, $R_4$ and $R_5$ are selected from the group consisting of H, $C_1$–$C_{16}$ aliphatic groups, $C_1$–$C_{16}$ cycloaliphatic groups, $C_1$–$C_{16}$ aromatic groups, and mixtures thereof.

27. The reactive compound of claim 1 wherein n' is greater than 1 and at least one of $R_3$, $R_4$ and $R_5$ are selected from the group consisting of $C_1$–$C_{16}$ aliphatic groups, $C_1$–$C_{16}$ cycloaliphatic groups, $C_1$–$C_{16}$ aromatic groups, and mixtures thereof.

28. The reactive compound of claim 27 wherein at least two of $R_3$, $R_4$ and $R_5$ are selected from the group consisting of $C_1$–$C_{16}$ aliphatic groups, $C_1$–$C_{16}$ cycloaliphatic groups, $C_1$–$C_{16}$ aromatic groups, and mixtures thereof.

29. The reactive compound of claim 28 wherein at least three of $R_3$, $R_4$ and $R_5$ are selected from the group consisting of $C_1$–$C_{16}$ aliphatic groups, $C_1$–$C_{16}$ cycloaliphatic groups, $C_1$–$C_{16}$ aromatic groups, and mixtures thereof.

30. A reactive compound comprising one or more structures of the formula:

$$X-\underset{\underset{R_2}{|}}{\overset{\overset{R_1}{|}}{C_n}}-\underset{\underset{R_0}{|}}{\overset{\overset{Y}{|}}{C}}-\underset{\underset{R_4}{|}}{\overset{\overset{R_3}{|}}{C_{n'}}}-R_5$$

wherein
 X is a primary carbamate group,
 Y is a hydroxy or halide group,
 n is an integer of 3 or more,
 n' is an integer of 1 or more, and
 $R_0$, $R_1$, $R_2$, $R_3$, $R_4$ and $R_5$ may be H or alkyl group,
with the provisos that
 (i) at least one of the $R_1$ or $R_2$ groups is not hydrogen, and
 (ii) in substantially all structures, primary carbamate group X is attached to a carbon atom having a lower degree of substitution than a carbon atom to which functional group Y is attached,
wherein the reactive compound is produced by a method comprising:
 providing a compound (a) having a functional group $F_i$ and functional group $F_{ii}$ separated by at least three carbon atoms, wherein:
  (1.) said functional groups $F_i$ and $F_{ii}$ are hydroxy or halide groups, and
  (2.) functional group $F_i$ is attached to a carbon atom having a lower degree of substitution than a carbon atom to which functional group $F_{ii}$ is attached
 providing one or more compounds (b) having at least one functional group (iii) reactive with functional group $F_{ii}$ to produce a primary carbamate group, and
 reacting compound (a) with a compound (b) to produce the reactive compound comprising one or more structures.

* * * * *